(12) United States Patent
Senegas

(10) Patent No.: US 6,572,617 B1
(45) Date of Patent: Jun. 3, 2003

(54) VERTEBRA IMPLANT

(75) Inventor: Jacques Senegas, Merignac (FR)

(73) Assignee: Stryker Spine (FR)

( * ) Notice: Subject to any disclaimer, the term of this patent is extended or adjusted under 35 U.S.C. 154(b) by 0 days.

(21) Appl. No.: 09/554,015
(22) PCT Filed: Nov. 6, 1998
(86) PCT No.: PCT/FR98/02378
§ 371 (c)(1), (2), (4) Date: Sep. 1, 2000
(87) PCT Pub. No.: WO99/23963
PCT Pub. Date: May 20, 1999

(30) Foreign Application Priority Data

Nov. 10, 1997 (FR) .............................. 97 14091

(51) Int. Cl.[7] .............................................. A61B 17/70
(52) U.S. Cl. .......................................... 606/61; 606/69
(58) Field of Search .............................. 606/53, 60, 61, 606/69, 70, 71, 72, 75, 87

(56) References Cited

U.S. PATENT DOCUMENTS 4,841,959 A * 6/1989 Ransford
5,662,655 A * 9/1997 Laboureau et al. ........... 606/75

FOREIGN PATENT DOCUMENTS

WO WO 97/09940 3/1997

OTHER PUBLICATIONS

E. Frank ET T. L. Keenen: "A Technique For Cervical Laminoplasty Using Mini Plates," British Journal of Neurosurgery, vol. 8, No. 2, 1994, pp. 197–199, XP002071037, see p. 197, right–hand column—p. 198, left–hand column; figures 1, 2.

* cited by examiner

Primary Examiner—David O. Reip
(74) Attorney, Agent, or Firm—Lerner, David, Littenberg, Krumholz & Mentlik, LLP

(57) ABSTRACT

A implant for a cervical vertebra comprises two branches adapted to extend respectively substantially along the two cervical laminae of a given cervical vertebra that have been spaced apart from each other after osteotomy of the laminae, and a rigid body interconnecting the two branches.

25 Claims, 2 Drawing Sheets

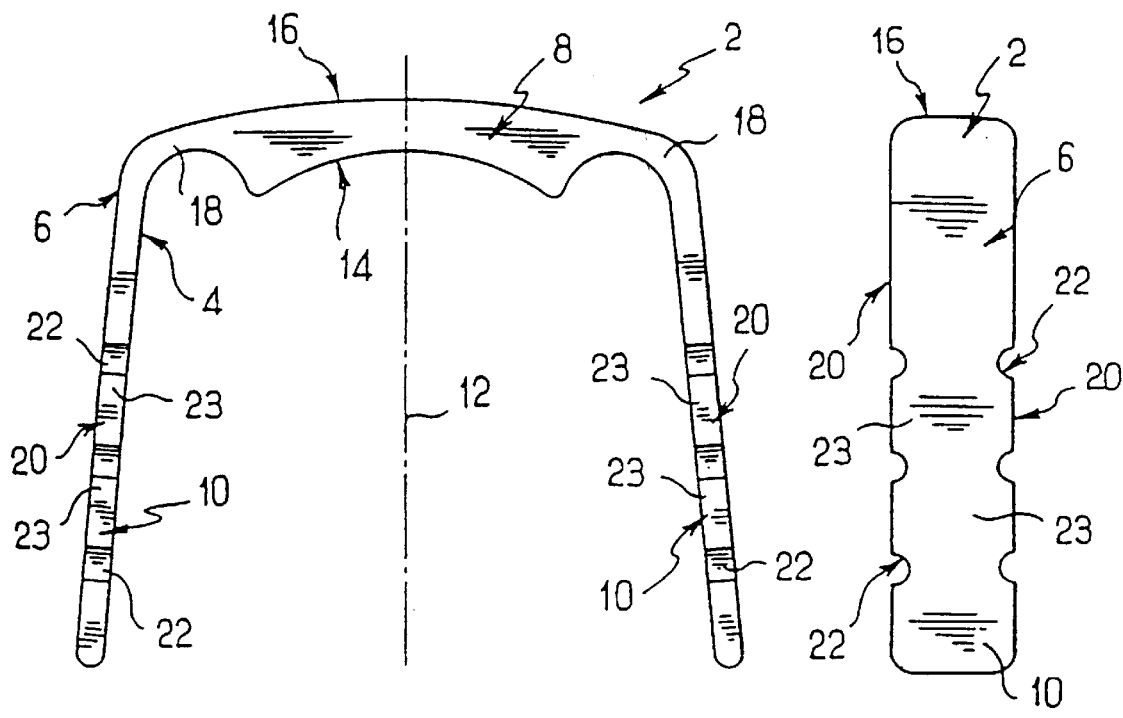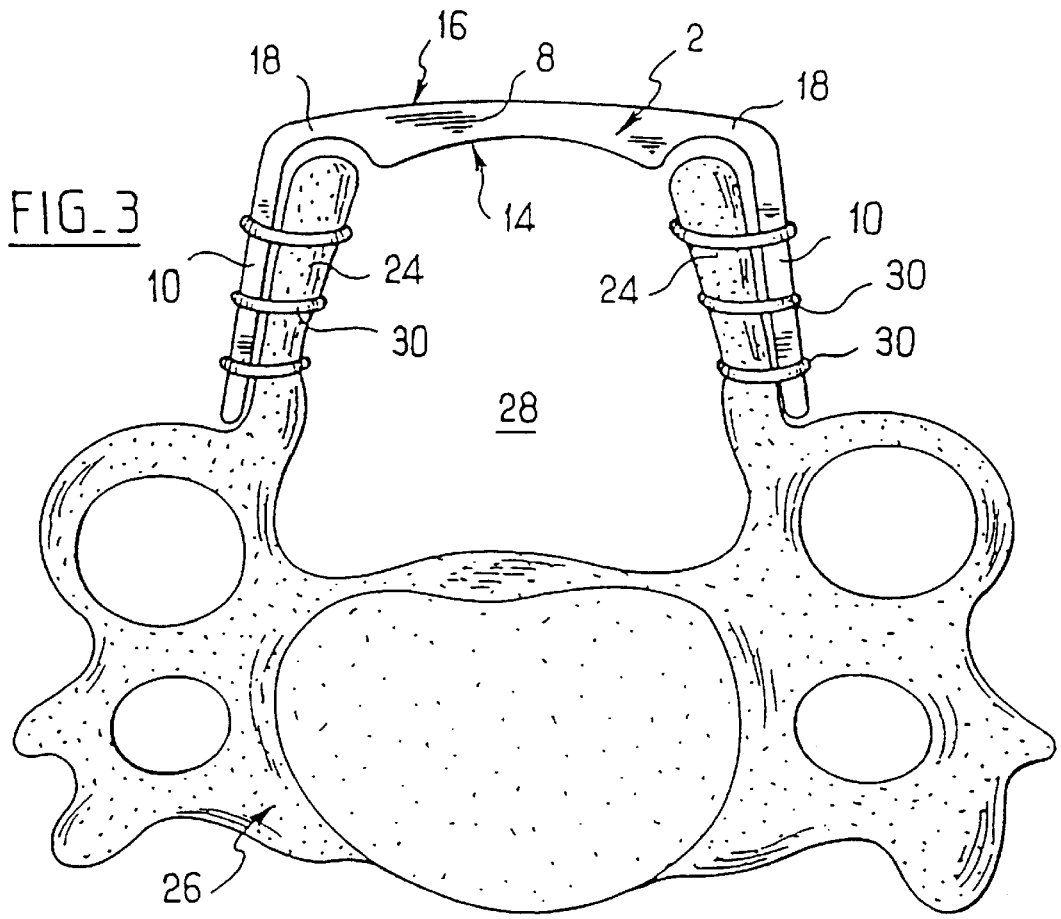

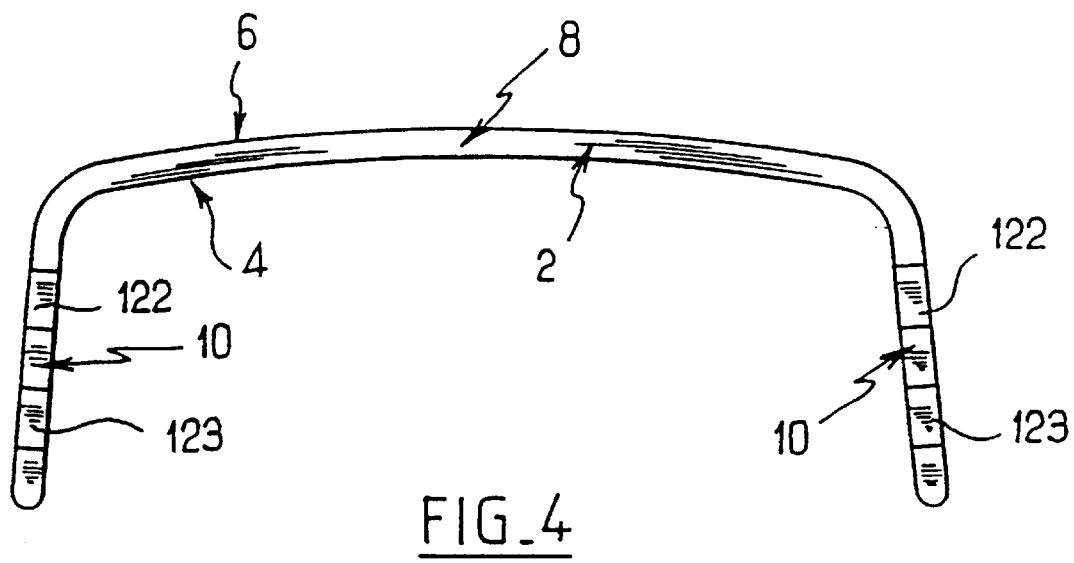
FIG_4
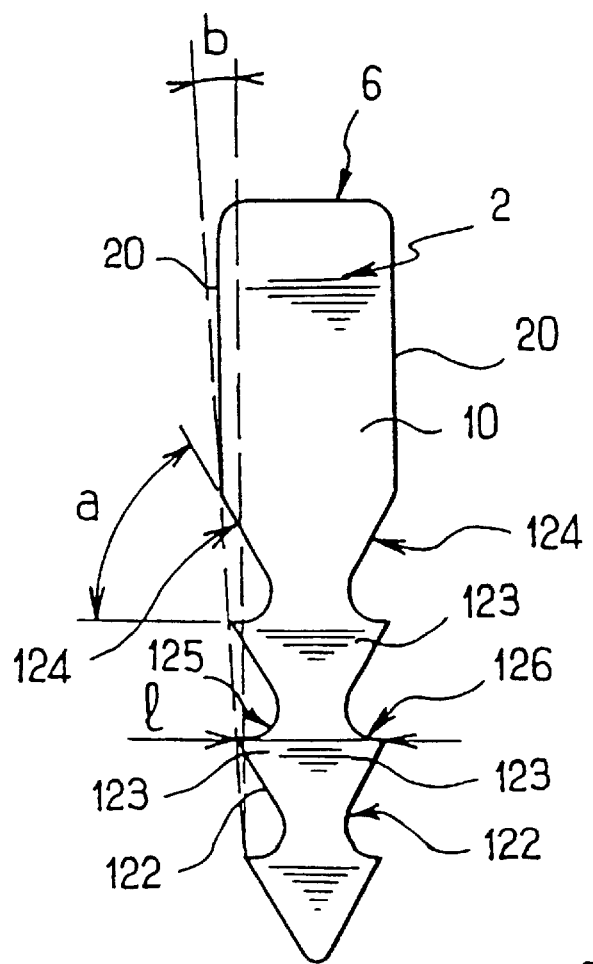
FIG_5

VERTEBRA IMPLANT

BACKGROUND OF THE INVENTION

The invention relates to cases of compression syndrome in the spine of the neck.

Compression syndrome in the cervical vertebrae can arise because of injury or of malformation.

SUMMARY OF THE INVENTION

An object of the invention is to provide a device for responding to cases of compression syndrome.

In order to achieve this object, the invention provides an implant for a cervical vertebra, the implant comprising two branches adapted to extend respectively substantially along the two cervical laminae of a given cervical vertebra that have been spaced apart from each other after osteotomy of the laminae, and a rigid body interconnection the two branches.

Thus, after osteotomy of the cervical laminae and after they have been spread rearwards, the branches of the implant can be fixed to the respective laminae to hold them apart, thereby putting an end to compression on the cavity.

Advantageously, the implant has a deformable link between the body and at least one of the branches.

Thus, the implant adapts appropriately to the morphology of the vertebra.

Advantageously, the link is elastically flexible.

Advantageously, the body has a zone of thickness that is reduced compared with the thickness of the remainder of the body and that defines the link.

Advantageously, the body is generally curved in shape, having a center of curvature situated on the same side as the branches.

Thus, the size of the implant is matched to the shape of the cavity.

Advantageously, the body has a curved inner face situated facing the branches and an outer face opposite from the branches, the inner face having curvature with a center of curvature that is situated on the same side as the branches and a radius of curvature that is smaller than the radius of curvature of the outer face.

Here again, the shape of the implant leaves the necessary volume for the cavity.

Advantageously, at least one of the branches has portions in relief.

Advantageously, the portions in relief form abutments preventing link elements that extend substantially perpendicularly to the longitudinal direction of the branch from moving along the branch.

This facilitates fixing the branches to the laminae and increases the lifetime of the fixings.

Advantageously, the portions in relief comprise notches.

Advantageously, the branches are suitable for being engaged in holes formed in the cervical laminae, and the portions in relief comprise barb-forming teeth.

Advantageously, the branch is of a width measured between the tips of the teeth that tapers towards the free end of the branch.

Advantageously, the portions in relief extend over two opposite longitudinal faces of the branch.

BRIEF DESCRIPTION OF THE DRAWINGS

Other characteristics and advantages of the invention will appear further on reading the following description of two preferred embodiments given as non-limiting examples. In the accompanying drawings:

FIGS. 1 and 2 are an elevation view and a side view of an implant constituting a first embodiment of the invention;

FIG. 3 is a view of the FIG. 1 implant installed on a vertebrae; and

FIGS. 4 and 5 are two views analogous to FIGS. 1 and 2 of an implant constituting a second embodiment of the invention.

DESCRIPTION OF THE PREFERRED EMBODIMENT

With reference to FIGS. 1 and 2, in a first embodiment, the implant 2 is generally in the form of a flat elongate bar having two plane faces 4 and 6 that are opposite each other, the bar being bent to give it a U-shape that comprises two branches 10 and a body 8 interconnecting the two branches. The bar is bent about two axes, corresponding to the bends, and parallel to the plane faces 4 and 6 which can thus be referred to respectively as the inner face and as an outer face. The implant has an axis of symmetry 12 passing through the middle of the body 8. The two branches 10 slope outwards, each away from said axis 12. The body 8 and the two branches 10 are of about the same length.

The shape of the body 8 is generally curved, having a center of curvature situated on the axis 12 and on the same side as the branches 10. An inside face 14 of the body has a radius of curvature that is smaller than the radius of curvature of an outside face 16 of the body opposite therefrom. The body 8 has two link zones 18 at its respective ends which are contiguous with the branches 10. The two zones 18 are of reduced thickness, i.e. they present thickness that is less than the thickness of the remainder of the body. Each of them provides an elastically flexible deformable link between the body 8 and a respective branch 10. These zones 18 of reduced thickness are defined by depressions in the inner face 4 serving to provide spaces for receiving the ends of the laminae of the vertebra.

Each branch 10 has two longitudinal edge faces 20, in which pairs of notches 22 are formed, the notches in each pair extending into the respective faces 20 at the same levels along the branch. By way of example, there are three pairs of notches 22 along each branch. Between them the notches 22 define flat-topped teeth 23.

To use the implant, osteotomy is performed in the two cervical laminae 24 of a cervical vertebra 26 so as to open up the cervical cavity 28 defined by the laminae. The laminae 24 are then spread apart from each other towards the back of the patient's body, e.g. until they slope towards each other only slightly, thereby eliminating the compression on the cavity 28.

The implant 2 is put into place. For this purpose, each branch 10 is pressed against a respective lamina 24 on an outside face of the lamina remote from other lamina. Each branch 10 is attached to the associate lamina 24 by binding means 30 which can be threads or tows of implantable material. These means are received in the respective pairs of notches 22, which prevent them from sliding along the associate branch 10. The implant 2 is thus secured at its implantation site in a manner that prevents it from moving. The implant serves to keep the laminae 24 spaced apart from each other.

With reference to FIGS. 4 and 5, in a second embodiment of the implant, the body 8 is of a length that is about three times the length of the branches 10. In addition, the body 8 is of a constant thickness over its entire length, which thickness is identical to the thickness of the branches 10. It is defined by the two faces 4 and 6 which are curved, concentrically and with the same radius of curvature.

Each branch 10 has notches 122 in its edge faces 20 defining pairs of teeth 123 that have sharp tops. Each tooth 123 has, on its side adjacent to the free end of the branch 10, a face 124 that slopes at an angle relative to the direction perpendicular to the longitudinal direction of the branch. The angle a is equal to 60°, for example. On its side adjacent to the body 8, each tooth 123 present a face 126 that is perpendicular to the longitudinal direction of the branch. At the bottom of each notch 122, the junction 125 between two faces 124 and 126 of adjacent teeth 123 is curved. In addition, the width l of the branch 10 corresponding to the distance between the tips of the teeth 123 in each pair decreases linearly from the end of the branch connected to the body towards the free end of the branch. The aligned tips of the three teeth 123 on each face 20 define a line which forms an angle b relative to the longitudinal direction of the branch 10. This angle b can be 3°, for example. The embodiment shown in FIGS. 2 and 4 is advantageously applied to cases where the two branches 10 are engaged in holes formed slantwise in the cervical laminae, the teeth 123 forming barbed plungers that serve to prevent said branches from escaping from the laminae by coming out of said holes.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An implant for cervical vertebra, the implant comprising first and second branches adapted to extend respectively substantially along an exposed surface of the two cervical laminae of a given cervical vertebra that have been spaced apart from each other after osteotomy of the laminae, a rigid body interconnecting the first and second branches, said first and second branches sloping outwardly away from an axis of symmetry passing through a middle of said rigid body and means engaging each of said first and second branches and said two laminae for attaching said implant to said vertebra.

2. The implant according to claim 1 wherein the implant has a deformable link between the body and at least one of the branches.

3. The implant according to claim 2 wherein that the link is elastically flexible.

4. The implant according to claim 1 wherein both said first and second branches extend from a side of said body and that the body is generally curved in shape, having a center of curvature situated on the same side as the branches.

5. The implant according to claim 1 wherein said means engaging said first and second branches for attaching are link elements that extend substantially perpendicularly to a longitudinal axis of at least one of said first and second branches.

6. The implant according to claim 5 wherein the at least one branch has portions in relief forming abutments preventing the link elements that extend substantially perpendicularly to the longitudinal axis of the branch from moving along the branch.

7. The implant according to claim 6 wherein the portions in relief comprise notches.

8. The implant according to claim 6 wherein the portions in relief extend over two opposite longitudinal faces of the at least one branch.

9. The implant according to claim 5 wherein the branches are suitable for being engaged in holes formed in the cervical laminae, and in that the portions in relief comprise barb-forming teeth.

10. The implant according to claim 9 wherein the branch is of a width measured between a tip of the teeth that tapers towards a free end of the branch.

11. The implant according to claim 1, wherein the body has a zone of thickness that is reduced compared with the thickness of the remainder of the body and that defines a link.

12. The implant according to claim 1, wherein the body has a curved inner face situated facing the branches and an outer face opposite from the branches, the inner face having curvature with a center of curvature that is situated on the same side as the branches and a radius of curvature that is smaller than the radius of curvature of the outer face.

13. An implant for cervical vertebra, the implant comprising first and second branches adapted to extend respectively substantially along an exposed surface of the two cervical laminae of a given cervical vertebra that have been spaced apart from each other after osteotomy of the laminae and a link having a rigid body interconnecting the first and second branches, wherein the body has a zone of thickness that is reduced compared with the thickness of the remainder of the body and that defines the link.

14. An implant for cervical vertebra, the implant comprising first and second branches adapted to extend respectively substantially along an exposed surface of the two cervical laminae of a given cervical vertebra that have been spaced apart from each other after osteotomy of the laminae and a rigid body interconnecting the first and second branches, said branches extending from a side of said rigid body wherein the body has a curved inner face situated facing the branches and an outer face opposite from the branches, the inner face having curvature with a center of curvature that is situated on the same side of said body from which the branches extend and having a radius of curvature that is smaller than a radius of curvature of the outer face.

15. A method for installing an implant on the spine, the implant comprising two branches and a body interconnecting the two branches, comprising:

(a) performing an osteotomy of the two laminae of a cervical vertebra of the spine;

(b) spreading the laminae apart from each other toward the back of the patient's body; and (c) affixing the branches to the respective laminae.

16. The method as set forth in claim 15 wherein said affixing of the branches to the respective laminae is accomplished by wrapping a binding around both the branches and the laminae.

17. The method as set forth in claim 16 wherein said binding is a thread of implantable material.

18. The method as set forth in claims 16 or 17 wherein said branches include notches for receiving the binding.

19. The method as set forth in claim 15 further including placing the branches against an outwardly facing surface of each laminae prior to affixing the branches thereto.

20. The method as set forth in claim 19 further including the step of deforming at least one branch with respect to said body prior to placing said implant on the laminae.

21. An implant for a vertebra comprising:

a body having first and second ends;

a first branch extending from said first end of said body and a second branch extending from said second end of said body, said branches extending away from a side of said body towards the vertebra for engaging an exposed surface of two laminae of said vertebrae;

a deformable portion connecting at least one of said branches to said body; and said first and second branches sloping outwardly away from an axis of symmetry passing through a middle of said rigid body and means engaging each of said first and second branches and said two laminae for attaching said implant to said vertebra.

22. The implant as set forth in claim 21 wherein the deformable portion is elastically deformable.

23. The implant as set forth in claim 21 wherein said body is curved with a center of curvature located on the same side as said branches.

24. The implant as set forth in claim 21 wherein said branches include notches.

25. The implant as set forth in claim 24 wherein said means for attaching includes a binding for engaging said notches.

* * * * *